United States Patent [19]

Yiannikouros et al.

[11] Patent Number: 5,352,781
[45] Date of Patent: Oct. 4, 1994

[54] PROCESS FOR PRECURSORS TO CALCITRIOL AND RELATED COMPOUNDS

[75] Inventors: George P. Yiannikouros, Westfield; Percy S. Manchand, Montclair, both of N.J.

[73] Assignee: Hoffmann-La Roche Inc., Nutley, N.J.

[21] Appl. No.: 35,141

[22] Filed: Mar. 19, 1993

Related U.S. Application Data

[60] Division of Ser. No. 955,540, Oct. 1, 1992, Pat. No. 5,225,569, which is a division of Ser. No. 848,881, Mar. 11, 1992, Pat. No. 5,182,393, which is a continuation of Ser. No. 742,796, Aug. 9, 1991, abandoned.

[51] Int. Cl.$^5$ .................................. C07C 401/00
[52] U.S. Cl. .................................. 540/4; 549/4; 549/53; 552/505; 552/541; 552/544; 552/546; 552/547; 552/548; 552/552; 552/653
[58] Field of Search .................. 540/4; 549/4, 53; 552/505, 541, 544, 546, 547, 548, 552, 653

[56] References Cited

U.S. PATENT DOCUMENTS

| | | |
|---|---|---|
| 3,856,780 | 12/1974 | Narwid et al. |
| 4,338,250 | 7/1982 | DeLuca et al. |
| 4,772,433 | 9/1988 | Hesse |
| 4,866,048 | 9/1989 | Calverly, et al. |
| 5,110,924 | 5/1992 | Halkes et al. .................. 544/233 |
| 5,182,393 | 1/1993 | Yiannikouros et al. .................. 549/4 |
| 5,218,109 | 6/1993 | Tsuji et al. .................. 540/4 |
| 5,225,569 | 7/1993 | Yiannikouros et al. .................. 549/4 |

OTHER PUBLICATIONS

Mascarenas, et al. Tetrahedron Letters, vol. 32, No. 4, p. 2813–2816 (1991).
Calverley, Tetrahedron, vol. 43, No. 20, pp. 4609–4619 (1987).
Mascarenas, et al. Tetrahedron, vol. 47, No. 20/21, pp. 3485–3498 (1991).
Andrews, et al. J. Org. Chem. vol. 51, pp. 4819–4828 (1986).
Marshall, et al. J. Org. Chem. vol. 51, pp. 1635–1637 (1986).
Yamada, et al. J. Org. Chem. vol. 48, pp. 3483–3488 (1983).
Schonecker, et al. Tetrahedron Letters, vol. 31, No. 9, pp. 1257–1260 (1990).

*Primary Examiner*—Johann Richter
*Assistant Examiner*—Kimberly J. Kestler
*Attorney, Agent, or Firm*—George M. Gould; William G. Isgro

[57] ABSTRACT

The process of the invention comprises reacting a C-22-halo-23,24-bisnorsteroid or C-22-halo-23,24-bisnor-9,10-secosteroid with a nickel complex of an electron withdrawing alkene of the formula

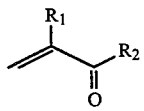

III wherein $R_1$ is hydrogen, hydroxycarbonyl, lower alkoxycarbonyl, lower alkylcarbonyl or unsubstituted or substituted lower alkyl, and $R_2$ is hydroxyl, lower alkoxy, or unsubstituted or substituted lower alkyl, to yield a C-25 or C-26 precursor of the formula

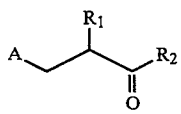

IV which is appropriately functionalized for conversion into the corresponding steroid or secosteroid by treatment as hereinafter described.

9 Claims, No Drawings

PROCESS FOR PRECURSORS TO CALCITRIOL AND RELATED COMPOUNDS

This is a divisional of U.S. Ser. No. 07/955,540 filed Oct. 1, 1992 now U.S. Pat. No. 5,225,569, which is a divisional of U.S. Ser. No. 07/848,881 filed Mar. 11, 1992, now U.S. Pat. No. 5,182,393, which is a continuation of U.S. Ser. No. 07/742,796 filed Aug. 9, 1991, now abandoned.

BRIEF SUMMARY OF THE INVENTION

The process of the invention comprises reacting a C-22-halo-23,24-bisnorsteroid or C-22-halo-23,24-bisnor-9,10-secosteroid with a nickel complex of an electron withdrawing alkene of the formula

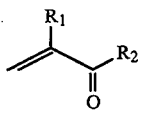
III wherein $R_1$ is hydrogen, hydroxycarbonyl, lower alkoxycarbonyl, lower alkylcarbonyl or unsubstituted or substituted lower alkyl, and $R_2$ is hydroxyl, lower alkoxy, or unsubstituted or substituted lower alkyl, to yield a C-25 or C-26 precursor of the formula

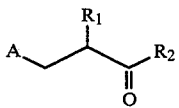
IV which is appropriately functionalized for conversion into the corresponding steroid or secosteroid by treatment as hereinafter described.

DETAILED DESCRIPTION OF THE INVENTION

The invention relates to a process for preparing precursors of the formula

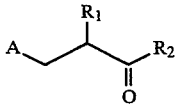
IV useful in the preparation of calcitriol and related compounds which comprises reacting a C-22-halo-23,24-bisnorsteroid or C-22-halo-23,24-bisnor-9,10-secosteroid, further characterized by the formula AX, wherein A is 23,24-bisnorsteroid or a 23,24,bisnor-9,10-secosteroid radical and X is halogen, with a nickel complex of an electron withdrawing alkene of the formula

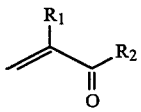
III wherein $R_1$ is hydrogen, hydroxycarbonyl, lower alkoxycarbonyl, lower alkylcarbonyl or unsubstituted or substituted lower alkyl, and $R_2$ is hydroxyl, lower alkoxy or unsubstituted or substituted lower alkyl, to yield a C-25 or C-26 precursor appropriately functionalized for conversion into the corresponding steroid or secosteroid by treatment as hereinafter described.

Preferably, in formulas III and IV, $R_1$ is hydrogen and $R_2$ is lower alkoxy or lower alkyl.

As used herein, the term "lower alkyl" denotes a straight or branched chain saturated hydrocarbon radical containing 1 to 7 carbon atoms, preferably from 1 to 4 carbon atoms, for example, methyl, ethyl, propyl, isopropyl, butyl, t-butyl, neopentyl, pentyl, heptyl and the like. The lower alkyl group may be substituted by, for example, hydroxyl or lower alkoxy. The term "lower alkoxy" denotes an alkyl ether in which the alkyl group is as described above, for example, methoxy, ethoxy, propoxy, pentoxy, and the like. As further used herein, the term halogen preferably includes iodine, bromine, and chlorine.

The term "protecting group" denotes a group for protecting a hydroxyl group which, upon acid catalyzed cleavage, hydrogenolysis or nucleophilic attack yields the free hydroxyl group. Suitable protecting groups are, for example, tetrahydropyranyl, benzyl, t-butyl or 4-methoxy-tetra-hydropyranyl. Other examples include benzhydryl, trityl, alpha-lower alkoxy-lower alkyl such as methoxymethyl, tri(lower alkyl) silyl, such as, trimethylsilyl, t-butyldiethylsilyl or t-butyldimethylsilyl.

The term "23,24-bisnorsteroid radical" denotes asteroid in which $C_{23}$ and $C_{24}$ and subsequent carbons are absent from the normal steroid side chain. The term "23,24-bisnorsecosteroid radical" denotes asteroid in which $C_{23}$ and $C_{24}$ and subsequent carbons are absent in the normal steroid side chain, and the $C_9$ and $C_{10}$ bond is absent. It is noted that in said steroids a free hydroxyl is protected for the purposes of this invention.

Exemplary of such steroid radicals are:

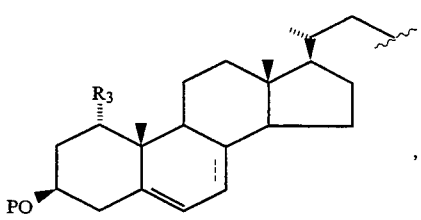

,

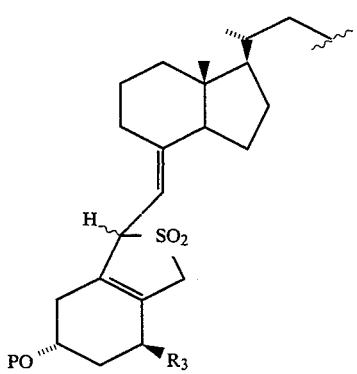

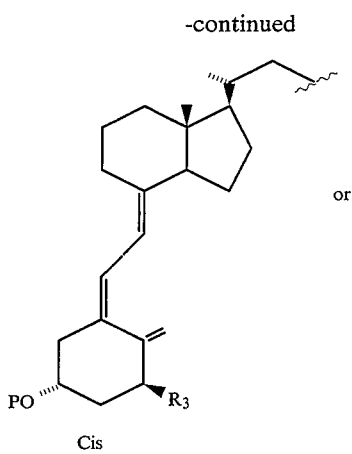

or

Cis

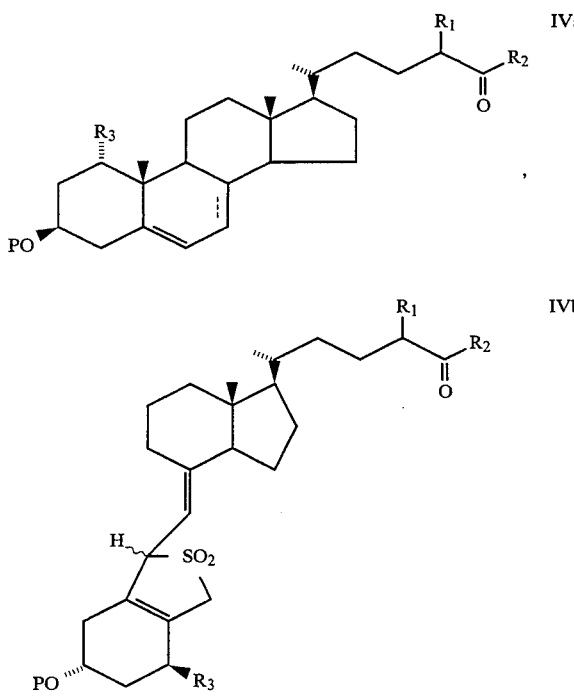

Trans wherein $R_3$ is hydrogen or OP, and P is hydrogen or a protecting group.

Exemplary of the compounds of formula IV are:

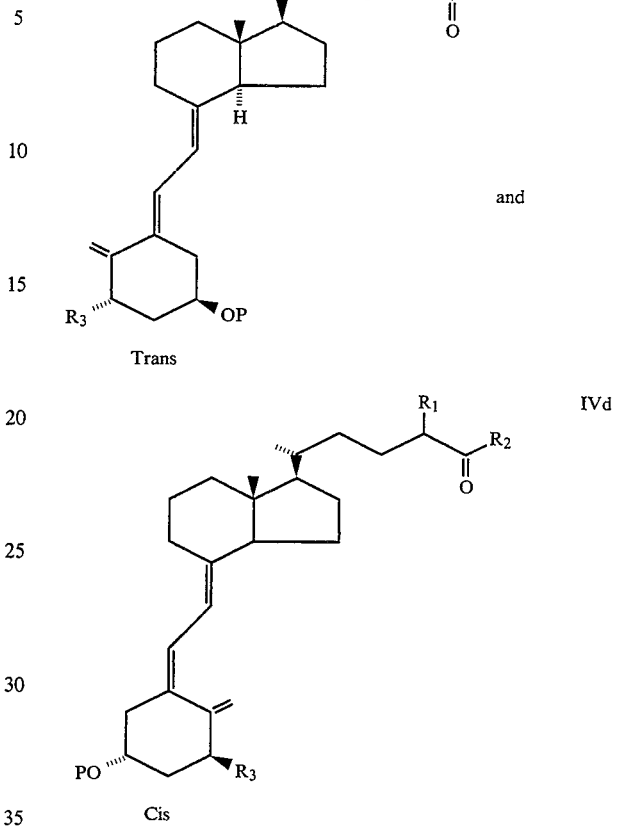

Trans

Cis wherein $R_1$, $R_2$, $R_3$, A and P are as previously described.

The compounds of formulas IVb and IVc also form part of this invention.

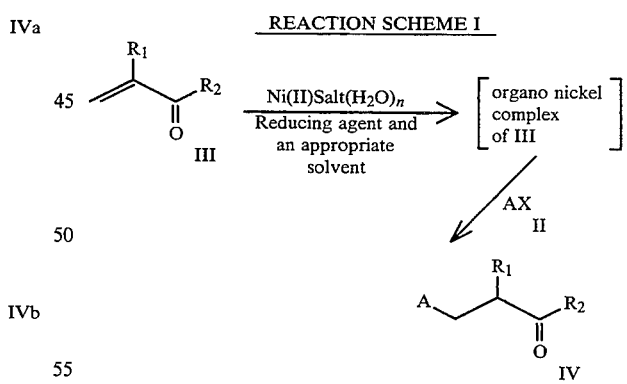

wherein $R_1$, $R_2$, A and X are as previously described, and n is an integer from 0 to 6, provided that, when n is 0, a proton source is required for the reaction.

In Reaction Scheme I, a compound of formula III, which are known compounds or can be prepared according to known procedures, is first reacted with a nickel (II) salt, for example, nickel acetonylacetonate, a nickel halide, such as, nickel chloride or the like, as its hydrate or, if unhydrated, in the presence of a proton source. This reaction is carried out in the presence of a reducing agent, such as, an alkaline earth metal or alkali metal, preferably, zinc metal, in an organic solvent which is also a ligand source, such as, pyridine or a mixture of solvents such as pyridine-tetrahydrofuran, pyridine-acetonitrile or the like, or in an organic solvent, such as, an alcohol, an ether or the like, and a ligand source, such as, triphenylphosphine or the like, conveniently, at a temperature in the range of 0° C.–150° C. and over a period of 5 minutes to 24 hours, to give a nickel complex of the compound of formula III.

The resulting complex is then treated, in situ, with a compound of formula II, which are known compounds or can be prepared according to known procedures, in a solvent or mixture of solvents as described above, conveniently, at temperature in the range of from 0° C. to 100° C. and over a period of 5 minutes to 24 hours, to give the corresponding compound of formula IV. The resulting compound of formula IV may be isolated and purified by known standard methods, such as, extraction followed by chromatography.

As the proton source, there can be used, for example, water, an ammonium salt, a pyridinium salt or the like.

The nickel (II) salt can be used in catalytic to stoichiometric quantities.

Exemplary of the compounds of formula II are compounds of the formulas

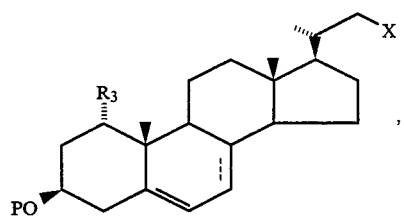

IIa

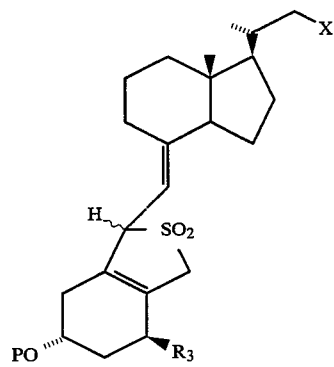

IIb and

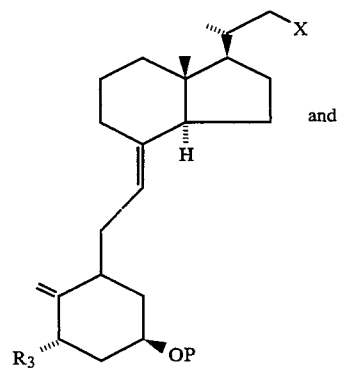

IIc

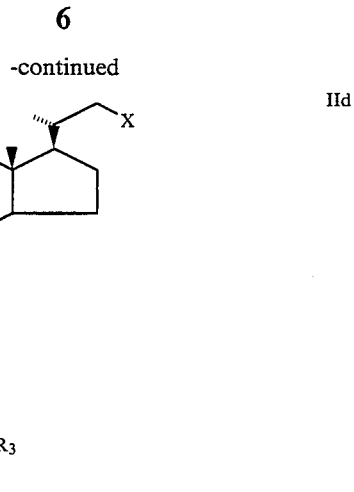

IId wherein $R_3$, P and X are as previously described, as well as,

1(S),3(R)-Bis-(tert-butyldimethylsilyloxy)-20(S)-(iodomethyl)-9,10-secopregna-5(Z),7(E),10(19)-triene;

1(S),3(R)-Bis-(tert-butyldimethylsilyloxy)-22-iodo-23,24-bisnor-5,7-cholestadiene;

3(R)-(tert-butyldimethylsilyloxy)-20(S)-(iodomethyl)-9,10-secopregna-5(Z),7(E),10(19)-triene; and the like.

SCHEME II

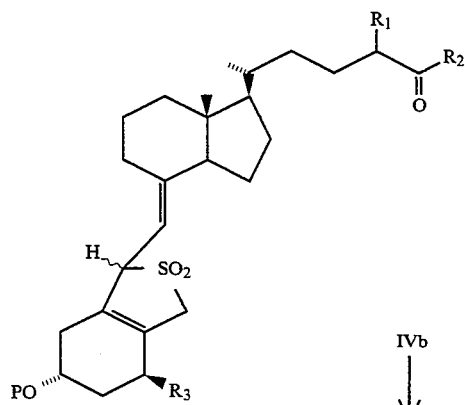

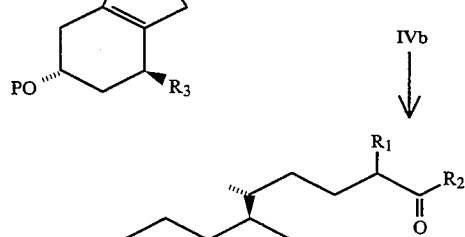

IVb

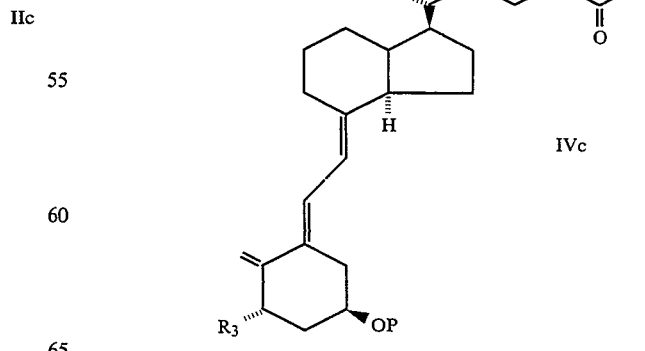

IVc

SCHEME III

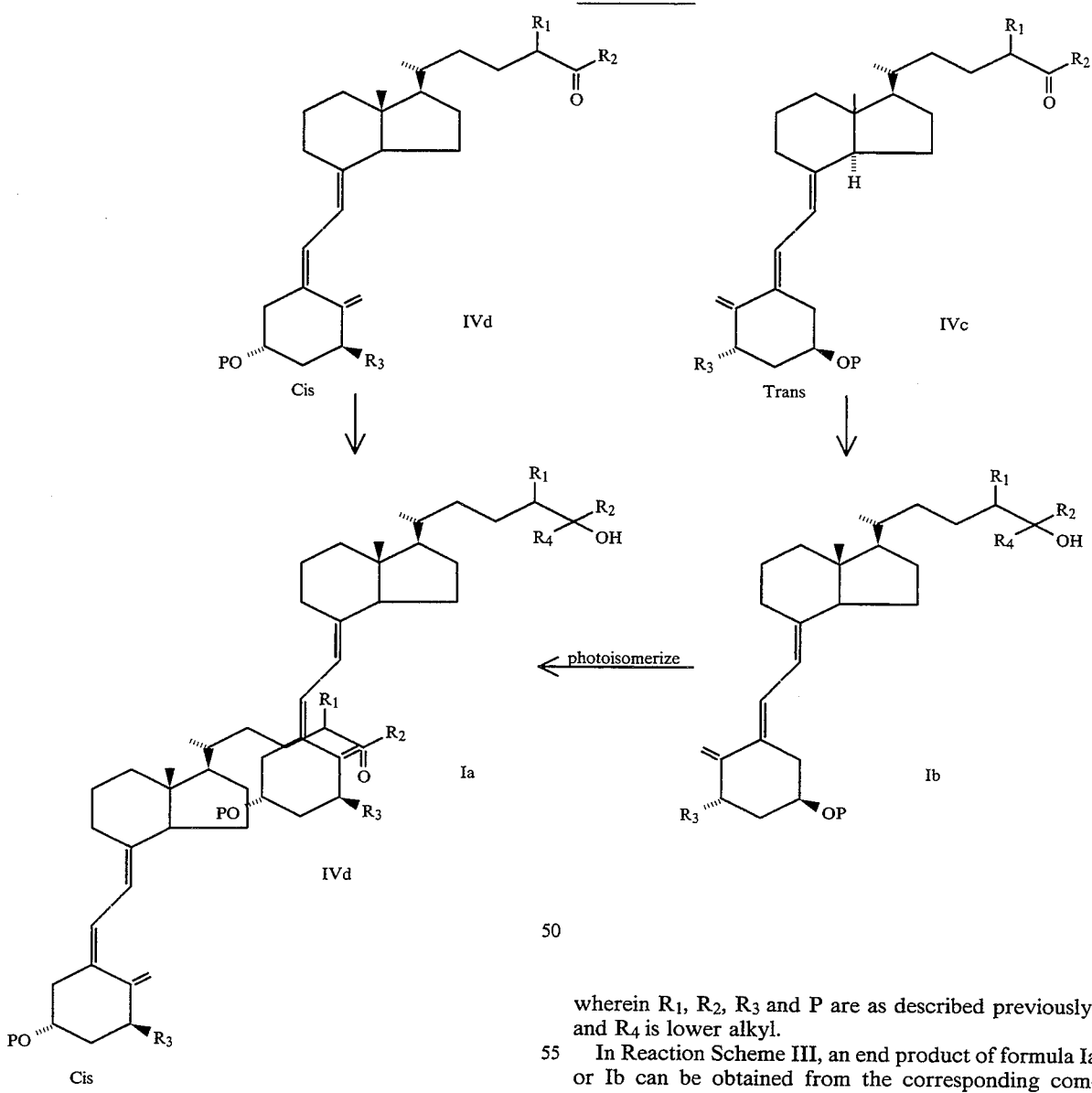

wherein $R_1$, $R_2$, $R_3$, and P are as previously described.

In Reaction Scheme II, the conversion of a compound of formula IVb into a compound of formula IVc can be carried out by the known method of cheletropic extrusion of sulfur dioxide, preferably by heating in the presence of a weak base, such as, sodium bicarbonate, or an organic base, such as, pyridine. The extrusion is carried out in a solvent, such as, ethanol or pyridine at a temperature in the range of 30° to 100° C. The resulting product of formula IVc is isolated by conventional methods, such as, extraction and chromatography.

A compound of formula IVc can be converted into the corresponding compound of formula IVd by photochemical isomerization using for example a 450 W medium pressure lamp, conveniently, at a temperature in the range of from 0°-50° C., in the presence of a photosensitizer, such as, 9-acetylanthracene or thioxanthen. As solvents for the isomerization, an alcohol, such as, methanol, a hydrocarbon, such as, hexane, and the like can be utilized.

wherein $R_1$, $R_2$, $R_3$ and P are as described previously, and $R_4$ is lower alkyl.

In Reaction Scheme III, an end product of formula Ia or Ib can be obtained from the corresponding compound of formula IVc or IVd by reaction with an organometallic reagent, such as, $R_4MgX$ or $R_4Li$, wherein $R_4$ is lower alkyl and X is halogen, in an ethereal solvent, such as, diethyl ether or tetrahydrofuran, at a temperature in the range of from about 0° C. to 70° C.

When P is a protecting group in a compound of formula Ia and Ib, deprotection of a compound of formula Ia leads to a corresponding vitamin $D_3$ compound. In the case of a compound of formula Ib, deprotection leads to the trans isomer, which can be photoisomerized, as described previously, to give the corresponding vitamin $D_3$ compound.

SCHEME IV

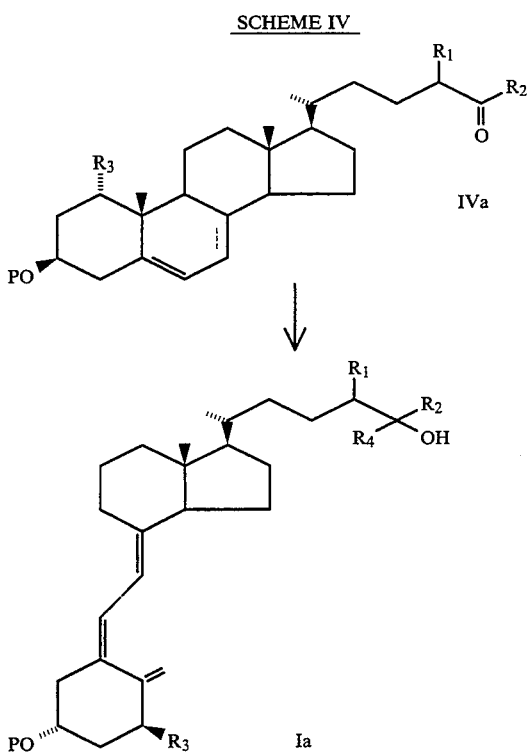

wherein $R_1$, $R_2$, $R_3$, $R_4$ and P are as previously described.

In Reaction Scheme IV, a compound of formula IVa, which are known compounds, which can be converted to the known compounds of formula Ia, as hereinafter described.

Such conversion involves reaction with an organometallic reagent followed by photolysis as described, for example, in:

(a) J. Tsuji et al, PCT Int. Appl. WO 9000560 (Jan. 25, 1990); C. A. 1990, 112, 217352g;

(b) B. Schoenecker et al, Tetrahedron Letters 1990, 31, 1257; Ger (East) DD 273,065 (Nov. 1, 1989); C. A. 1990, 112, 217351 f;

(c) Schoenecker et al, Ger (East) DD 268,956 (6/14/1989) C. A. 1990, 112, 1192426b; and (d) Fassler et al, Ger (East) DD 272,068 C. A. 1990, 112, 1988951.

The protecting groups can be removed by acid catalyzed cleavage, which is carried out by treatment with an organic or inorganic acid. Among the preferred inorganic acids are the mineral acids, such as, sulfuric acid, hydrohalic acid, or the like. Among the preferred organic acids are lower alkanoic acids, such as, acetic acid, paratoluenesulfonic acid, or the like. The acid catalyzed cleavage can be carried out in an aqueous medium or in an organic solvent medium. Where an organic acid or alcohol is utilized, the organic acid or alcohol can be the solvent medium. In the case of tetrahydropyranyl ethers, the cleavage is generally carried out in an aqueous medium. In carrying out such cleavage, temperature and pressure are not critical and this reaction can be carried out at room temperature.

In the case of nucleophilic cleavage of silyl protecting groups, nucleophilics such as a fluoride, a bromide, an iodide may be used according to known procedures.

The examples which follow further describes the invention. All temperatures are given in degrees Centigrade.

EXAMPLE 1

6(R,S)-$SO_2$ adduct of 9,10-seco-3-(tertbutyldimethylsilyloxy)-20-(S)-(iodomethyl)pregna-5(E), 7(E), 10(19)-triene To a solution of 50 g of the $SO_2$ adducts of 9,10-seco-3β-(tertbutyldimethylsilyloxy)-20-(S)-(hydroxymethyl)-pregna-5(E), 7(E), 10(19)-triene, which was prepared according to the method of Hesse (U.S. Pat. No. 4,772,433, Sep. 20, 1988) in 580 mL of dichloromethane was added 20.5 g of imidazole and 60 g of triphenylphosphine. The reaction mixture was cooled to $-10°$ C. under argon and 58 g of iodine was added portionwise keeping the reaction temperature below 10° C., over 20 minutes. The mixture was stirred for 0.5 hour and then the cooling bath was removed and stirring continued for 2 hours; tlc indicated that the reaction was complete. 15 mL of ethanol was added and the mixture was stirred for 1 hour. To this mixture was then added 15 g of sodium thiosulfate pentahydrate in 10 mL $H_2O$ to quench the excess iodine, and stirred for 0.5 hour. The solvent was removed in vacuo to dryness. The residue was slurried with 1.0 L of diethyl ether. The ether extract was decanted and then followed by additional 2×750 mL of ether extracts. The combined extracts were washed with 750 mL 1:1 brine-$H_2O$ and then dried ($Na_2SO_4$) and evaporated in vacuo to afford 60 g of crude C-22-iodo-$SO_2$-adduct t-butyldimethylsilyl ether. This was dissolved in 50 mL of 1:1 ethyl acetate-hexane and applied to 800 g of silica gel (200–400 mesh) column packed in 5% ethyl acetate in hexane. Elution at 4 psi air pressure with10×500 mL of 5% ethyl acetate in hexane, and 10×1.0 L of 10% ethyl acetate hexane. Fractions 4–20 were combined and evaporated in vacuo, to afford 50 g (71% yield) of 6(R,S)-$SO_2$ adduct of 9,10-seco-3-(tertbutyldimethylsilyloxy)-20-(S)-(iodomethyl)pregna-5(E), 7(E), 10(19)-triene as a light yellow foam. $^1$HNMR ($CDCl_3$) δ 0.05 (6H, $Me_2Si$) 0.60/0.69 (3H, $CH_3$-18), 0.90 (9H, t-BuSi), 1.02/1.06 (3H, d, J=7 Hz,$CH_3$-21), 3.20–3.30 (2H, m, $CH_2I$), 3.65 (2H, br s, $CH_2SO_2$), 4.00 (1H, br s, CHOSi), 4.58 (1H, d of d, J=2 and 7 Hz, CH-6) 4.72 (1H, d of d, J=2 and 7 Hz, CH-7).

EXAMPLE 2

6(R,S)-$SO_2$ adduct of 1(S),3(R)--Bis(tert-butyldimethylsilyloxy)-20(S)-(hydroxymethyl)-9,10-secopregna-5(E),7(E),10(19)-triene A mixture of (63.0 g) of the $SO_2$ adducts [(6S)- and 6(R)] of 1(S), 3(R)-Bis(tert-butyldimethylsilyloxy)-9,10-secoergosta. 5,7(E), 10(19),22(E)-tetraene (prepared according to the method of Calverley, Tetrahedron, 1987, Vol. 43,4609) in 450 mL of $CH_2Cl_2$ and 150 mL of methane was cooled to $-10°$ C. and ozonized for 10 minutes. The mixture was purged with argon treated with 10.25 g of powdered sodium borohydride, and then allowed to warm to room temperature. Stirring was continued at room temperature for 2.0 hours and the mixture was concentrated in vacuo to dryness. The residue was treated cautiously with a mixture of 350 mL of hydrochloric acid and 250 mL of ethyl acetate. The organic phase was separated, and the aqueous phase was re-extracted with 250 mL of ethyl acetate. The combined organic extracts were washed with 150 mL of saturated brine, dried (MgSO$_4$), filtered and evaporated to give 65.4 g of a pale yellow glass. Chromatography of this over 500 g of silica (230–400 mesh) with 3.6 L of 10% ethyl acetate in hexane, 3.6 L of 15% ethyl acetate in hexane, 5.4 L of 20% ethyl acetate in hexane, and 2 L of 25% ethyl acetate gave 42.64 g (85.5% yield) of the desired 6(R,S)-SO$_2$ adduct of 1(S),3(R)-Bis(tertbutyldimethylsilyloxy)-20(S)-(hydroxymethyl)-9,10-secopregna-5(E),7(E),10(19)-triene. A pure sample of the major isomer was obtained as a glass: mp 100°–103° C.; $[\alpha]^{25}D + 2.54°$ (CHCl$_3$, C=1.026); UV (EtOH) 203 ($\epsilon$=20,880) nm; IR (CHCl$_3$) 3625 cm$^{-1}$; $^1$H NMR (CDCl$_3$) δ 0.05 (2×Me$_2$Si), 0.65 (3 H, s, CH$_3$-18), 0.85 (2 x-t-BuSi), 1.05 (3H, d, J=7 Hz, CH$_3$-21), 3.40 (1H, d of d, J=2 and 7 Hz, CH$_A$ of CH$_2$OH) 3.60 (1 H, D, CH$_A$ of CH$_2$SO$_2$), 3.65 (1H, d of d, CH$_B$ of CH$_2$OH), 3.95 (1H, d of d, CH$_2$SO$_2$), 4.20 (1H, br s, CHOSi), 4.37 (1H, d, CH-6), 4.71 (1H, d, CH-7); MS m/z 574 (M-SO$_2$). Anal. Calcd for C$_{34}$H$_{62}$O$_5$ SSi$_2$: C,63.90; H,9.98; S,5.02. Found: C, 64.29;H,9-93;S,4.75.

EXAMPLE 3

6(R,S)-SO$_2$ adduct of 1(S),3(R)-Bis(tert-butyldimethylsilyloxy)-20(S)-(iodomethyl)-pregna-5(E),7(E),10(19)-triene A stirred solution of 19.5 g of imidazole and 36.61 g of triphenylphosphine in 300 mL of dichloromethane was treated with 33.1 g of iodine. The mixture was stirred at 10° C. for 15 minutes and treated with a solution of 41.64 g the epimeric alcohols (prepared in Example 2) in 200 mL of methylene chloride. Stirring was continued at room temperature for 2.5 hours, and the mixture was filtered. The filtrate was washed with 400 mL of 2% sodium thiosulfate, 200 mL of 0.5N hydrochloric acid, 200 mL of saturated brine, dried (MgSO$_4$), and evaporated to give an off-white solid, which was stirred with 400 mL of ether for 15 minutes (to remove triphenylphosphine oxide) and filtered. The filtrate was evaporated to give 53.7 g of crude mixture of 6S and 6R epimeric iodides. Chromatography (under 5 psi pressure) on 475 g of silica gel (230–400 mesh) with 1 L of hexane, 3.6 L of 5% ethyl acetate in hexane, and 3.6 L of 10% ethyl acetate in hexane, collecting 200 mL fractions, gave 40.79 g of 6(R,S)-SO$_2$ adduct of 1(S),3(R)-Bis(tert-butyldimethylsilyloxy)-20(S)-(iodomethyl)-pregna-5(E),7(E),10(19)-triene. Pure samples of each of the diastereomers (isomer A and isomer B) were isolated from the above chromatography and characterized as follows. Isomer A: amorphous solid, mp 78°–82° C., $[\alpha]^{25}D + 31.94°$ (CHCl$_3$, C=1.00) UV (EtOH) 201 ($\epsilon$=23,100); $^1$H NMR (CDCl$_3$) δ0.05 (2 x Me$_2$Si), 0.70 (3H, s, CH$_3$-18), 0.90 (2 x t-BuSi), 1.03 (3H, d, J=6 Hz, CH$_3$-21), 3.21 (1H, d of d, CH$_A$ of CH$_2$I), 3.32, (1H, d of d, CH$_B$ of CH$_2$ I), 3.61 (1H, d, CH$_A$ of CH$_2$SO$_2$), 3.92 (1H, d, CH$_B$ of CH$_2$SO$_2$), 4.20 (1H, CHOSi), 4.36 (1H, CHOSi), 4.65 (1H, d, CHSO$_2$), 4.70 (1H, CH-7); MS m/z 552 (M-SO$_2$-132). Anal. Calcd for C$_{34}$H$_{61}$ IO$_4$SSi$_2$: C,54.52; H, 8.21; S, 4.28; I, 16.94. Found: C, 54, H,8.41; S,4.50; I, 17.19. Isomer B Foam: $[\alpha]^{25}D - 12.35°$ (CHCl$_3$, C=0.8904); Anal. Calcd. for C$_{34}$H$_{61}$ IO$_4$ SSi$_2$: C, 54.52; H, 8.21; S, 4.28; I, 16.94. Found: C, 54.48; H, 8.46; S, 4.38; I, 17.23.

EXAMPLE 4

1(S),3(R)-Bis-(tert-butyldimethylsilyloxy)-20(S)-(hydroxymethyl)-9,10-secopregna-5(E),7(E),10(19) triene A 250-mL, round-bottomed flash equipped with a condenser capped with an argon inlet bubbler and containing a magnetic stirrer was charged with 5.5 g (8.6 mmol) of alcohol from Example 2 in 56 mL of 95% ethanol (2B) and the mixture was stirred at reflux for 5 hours. It was then concentrated under vacuum (water aspirator) to dryness, diluted with 150 mL of hexane and filtered. The filter cake was washed some hexane and the combined filtrate and washing were dried (MgSO$_4$), filtered and evaporated to give 4.53 g of a thick yellow oil. This was chromatographed on 86 g of flash silica gel (40 μm) packed in hexane with 2%, 3%, and 5% ethyl acetate in hexane, monitoring the progress of the chromatography by TLC (25% ethyl acetate in hexane). The appropriate fractions were combined and the solvents were removed by evaporation to give 1.65 g of 1(S),3(R)-bis-(tert-butyldimethylsilyloxy)-20(S)-(hydroxymethyl)-9,10-secopregna-5(E),-7(E),10(19) triene as a white solid: mp 116°–117° C., $[\alpha]^{25}D + 48.20°$ (CHCl$_3$, C=1.114); UV (EtOH) 269 ($\epsilon$=23,600) nm; IR (CHCl$_3$) 3625 cm$^{-1}$;$^1$H NMR (CDCl$_3$) 0.60 (12 H, 2 x SiMe$_2$). 0.57 (3H, s, CH$_3$-18), 0.86 (9 H, s, t-BuSi). 0.90 (9H, s, t-BuSi), 1.06 (3H, d, J=6 Hz, CH$_3$-21), 3.40 (1H, d of d, J=11 and 3 Hz, H$_A$ of CH$_2$OH), 3.66 (1H, d of d, J=11 and 3 Hz, H$_B$ of CH$_2$OH), 4.21 (1H, br s, CHOSi), 4.53 (1H, br s, CHOSi). 4.94 (1H, s, CH-19), 4.99 (1H, s, CH-19), 5.83 (1H, d, J=11 Hz, CH-7), 6.45 (1H, d, J=11 Hz, CH-6); MS m/z 574 (M+, 5). Anal. Calcd for C$_{34}$H$_{62}$O$_3$Si$_2$: C, 71.02; H, 10.87. Found: C, 71.04; H, 10.99.

EXAMPLE 5

1(S),3(R)-Bis-(tert-butyldimethylsilyloxy)-20(S)-(iodomethyl)-9,10-secopregna-5(E),7(E),10(19)-triene A 100-mL, 3-necked round-bottomed flask equipped with an argon inlet bubbler, and addition funnel, and containing a magnetic stirrer bar was charged with 0.861 g of imidazole, 1.66 g of triphenylphosphine, 20 mL of methylene chloride, and 1.46 g of iodine. The mixture was stirred at room temperature for 15 minutes, cooled to 10° C. and treated with a solution of 1.65 g of the alcohol from Example 4 in 10 mL of methylene chloride. Stirring was continued at room temperature for 1.5 hours, and the mixture was filtered. The filter cake was washed with 20 mL of methylene chloride and the combined filtrate and washing were washed with 30 mL of cold (~10° C.) 0.5N hydrochloric acid, 2×50 mL of saturated brine, dried (MgSO$_4$) and evaporated to give a semi-solid. This was slurried with 50 mL of ether, filtered (to remove triphenylphosphine oxide), and the filtrate was concentrated in vacuo to give 2.74 g of a gum. Flash chromatography over 45 g of silica (40 μm), which was packed in hexane, collection of the appropriate fractions, and evaporation gave a gum which was dried under high vacuum (0.2 mm Hg) to give 172 g of 1(S),3(R)-bis-(tert-butyldimethylsilyloxy)-20(S)-(iodomethyl)-9,10-secopregna-5(E),7(E),10(19)-triene as a foam $[\alpha]^{25}D + 24.99°$ (CHCl$_3$, C=1.0682) UV (EtOH) 267 (δ=21,600) nm; $^1$H NMR δ 0.05 (12H, 2 x SIMe$_2$), 0.58 (3 H, s, CH$_3$-18), 0.90 (18 H, (2x t-BuSi), 1.05 (3H, d, J=6 Hz, CH$_3$-21), 3.20 (1H, d of d, CH$_A$ of CH$_2$I), 3.33 (1H, d, CH$_B$ of CH$_2$I), 4.22 (1H, br s, CHOSi), 4.55 (1H, br s, CHOSi), 4.94 (1H, s, CH$_A$ of CH$_2$-19), 4.99 (1H, s, CH$_B$ of CH$_2$-19), 5.82 (1H, d, J=12 Hz, CH-7), 6.47 (1H, d, J=12 Hz, CH-6).

EXAMPLE 6

3β-(Isopropyldimethylsilyloxy)-22-iodo-23,24-bisnor-cholesta-5-ene

To a stirred solution of 2.5 g of 3β-(Isopropyldimethylsilyloxy)-22-hydroxy-23,24-bisnorcholesta-5-ene in 50 mL methylene chloride was added 2.62 g (10 mmol) of triphenylphosphine, 2.54 g (10 mmol) of iodine, and 1.02 g (15 mmol) of imidazole. The mixture was stirred at room temperature for 1.5 hours, concentrated and the residue was diluted with diethyl ether. Filtration and evaporation of the filtrate gave 3.5 g 3β-(Isopropyldimethylsilyloxy)-22-iodo-23,24-bisnor-cholesta-5 -ene, which was used without further purification in the next step (Example 7).

EXAMPLE 7

Ethyl 3β-(Isopropyldimethylsilyloxy)-26,27-bisnorcholesta-5-ene-25-oate

A mixture of 0.65 g of zinc powder, 1.2 g of nickel chloride hexahydrate, and 2.0 g (20 mmol) of ethyl acrylate in 10 mL of a 1:1 mixture of pyridine and tetrahydrofuran was stirred under argon at 65° C. for 30 minutes and then cooled to 35° C. A solution of 3.5 g of the iodide from Example 6 in 10 nil of a 1:1 mixture of pyridine and tetrahydrofuran was then added to the reaction mixture during 5 minutes. The mixture was stirred at 35° C. for 2 hours and then diluted with 100 mL of ethyl acetate. The mixture was washed with 2×50 mL of a solution consisting of 8% EDTA and 8% sodium bicarbonate, 2×50 mL of saturated brine, dried (Na$_2$SO$_4$), filtered, and evaporated to give a gum, which was purified by chromatography over silica gel to give ethyl 3β-(Isopropyldimethylsilyloxy)-26,27-bisnor-cholesta-5-ene-25-oate: IR (CHCl$_3$) 1725 (ester) cm$^{-1}$; $^1$H NMR (CDCl$_3$) δ 0.03 (Me$_2$Si) 0.65 (s, CH$_3$, CH$_3$-18), 0.72 (6H, s, 2x CH$_3$), 0.85 (6H, d, Me$_2$CH), 0.92 (d, CH$_3$-21) 0.95 (3 H, s, CH$_3$-19), 1.25 (CH$_3$, t, J=7 Hz) 3.48 (1H, m, CH-3), 4.11 (2H, q, J=7 Hz, CH$_2$O), 5.3 (1H, d, J=2 Hz, CH-6).

EXAMPLE 8

1α, 3β-Bis(tertbutyldimethylsilyloxy)-22-iodo-23,24-bisnor-cholesta-5-ene

A solution of 3.0 g of 1α,3β-bis(tertbutyldimethylsilyloxy)-22-(p-tolysulfonyloxy)-23,24-bisnor-cholesta-5-ene, prepared from the corresponding C$_{22}$ alcohol in 17 mL of acetone and 8 mL of dimethylsulfoxide was treated with 1.5 g of sodium iodide and the mixture was stirred at reflux for 18 hours. It was cooled to room temperature, diluted with 30 mL of water, and extracted with 70 mL of ethyl acetate. The combined extracts were washed with 2×50 mL of saturated brine, dried (MgSO$_4$), and evaporated to give 2.75 g of a solid, which was crystalized from a mixture of ether-methanol (1:2) to give 1α, 3β-bis(tertbutyldimethylsilyloxy)-22-iodo-23,24-bisnorcholesta-5-ene as colorless crystals, mp 144°-146° C.; [α]$_D$+20.38° (CHCl$_3$, C=0.927). Anal. Calcd. for C$_{34}$H$_{63}$IO$_2$Si$_2$: C, 59.45; H, 9.24; I, 18.47. Found: C, 59.54; H, 9.29; I, 18.17.

EXAMPLE 9

Ethyl 1α,3β-Bis-(tert-butyldimethylsilyloxy)-26,27-bisnor-cholesta-5 -ene-25-oate A stirred mixture of 250 mg of nickel chloride hexahydrate 350 mg of zinc dust and 0.5 mL of ethyl acrylate in 1.5 mL of tetrahydrofuran and 1.0 mL of pyridine was stirred at 60° C. for 25 minutes and then cooled to room temperature. To the resulting brick-red mixture was added 500 mg of the iodide in 2 mL of tetrahydrofuran and stirring was continued at room temperature overnight followed by heating at 50° C. for 4 hours. The mixture was diluted with 75 mL of ethyl acetate and filtered over Celite, and the filtrate was washed with 2×25 mL of saturated brine, dried (MgSO$_4$) and evaporated to give 540 mg of a gum. Chromatography of this over 20 g of silica gel (70–230 mesh) with 25% ethyl acetate in hexane followed by crystallization from ether-methanol to give ethyl 1α,3β-Bis-(tert-butyldimethylsilyloxy)-26,27-bisnorcholesta-5-ene-25-oate 330 mg (68.5% yield), mp 97°–100° C.; [α]$^{25}$D +13.48° (CHCl$_3$, C=0.986). Anal. Calcd for C$_{39}$H$_{72}$O$_4$Si$_2$: C, 70.85; H, 10.98. Found: C, 70.47; H, 10.85.

EXAMPLE 10

6(R,S)-SO$_2$ adduct of Ethyl 3(R)-(tertbutyldimethylsilyloxy)-9,10-seco-26,27-bis-nor-cholesta-5(E),7(E),10(19)-trien-25-oate A 500 mL three-neck flask equipped with a magnetic stirrer, and gas bubbler was charged with 13.1 g of zinc dust. To this was added 60 mL of a 1:1 mixture of tetrahydrofuran-pyridine, and 9.5 g of nickel chloride hexahydrate and 19.5 mL of ethyl acrylate. This mixture was then heated to 65° C. while being stirred under argon for 30 minutes to afford a reddish brown solution. The mixture was cooled to 30° C. and a solution of 50 g of the C-22-iodo SO$_2$ adduct t-butyldimethylsilyl ether (from Example 1) in 1:1 THF-pyridine was added over 1 hour at a rate so as to maintain the reaction temperature below 45° C. The mixture was stirred at ambient temperature for 2.5 hours. TLC (7:3 hexane-ethyl acetate) indicated that the reaction was complete. The mixture was filtered through a Celite pad and rinsed with 2×100 mL of ethyl acetate- The filtrate was concentrated to a third volume and then 1.5 L ethyl acetate added. This was then washed with 4×100 mL of EDTA solution (80 g EDTA/80 g NaHCO$_3$ diluted to 1.0 L), 2×100 mL of 1:1 brine-water, 2×100 mL saturated brine, dried (Na$_2$SO$_4$), evaporated in vacuo to afford 39 g (83% yield) of 6(R,S)-SO$_2$ adduct of ethyl 3(R)-(tertbutyldimethylsilyloxy)-9,10-seco-26,27-bis-nor-cholesta-5(E),7(E),10(19)-trien-25-oate. This material was used as such in the next step without further purification.

EXAMPLE 11

Ethyl (3R)-(tertbutyldimethylsilyloxy)-9,10-seco-26,27-bis-norcholesta-5(E),7-(E),10(19)-trien-25-oate 39 g of C-25-ethyl ester SO$_2$ adduct t-butyldimethylsilyl ether (from Example 10), 35 g of sodium bicarbonate and 500 mL of 95% ethanol was heated at reflux under argon for 2 hours. After cooling, the insolubles were removed by filtration and rinsed with 2×150 mL of EtOAc. The filtrate and washings were evaporated and the residue was taken up in 1.0 L of ethyl acetate. This was washed with 3×500 mL of 1:1 brine-water and 500 mL of brine, dried (Na$_2$SO$_4$), and evaporated to dryness to afford 43 g of crude product. This was dissolved in 30 mL of ethyl acetate and applied to 80 g of flash silica (200–400 mesh) pre-packed in 5% ethyl acetate in hexane. Elution at 4 psi air pressure with 10×500 mL of 5% ethyl acetate in hexane (TLC in 4:1 hexane/EtOAc). Fractions 4–7 were combined and evaporated in vacuo, and finally at 0.5 mm Hg for 2 hours, to afford 31 g (89%) yield of ethyl (3R)-(tertbutyldimethylsilyloxy)-9,10-seco-26,27-bisnor-cholesta-5(E),7-(E),10(19)-trien-25-oate as a colorless oil. $^1$H NMR (CDCl$_3$) δ 0.05 (6H, SiMe$_2$), 0.55 (3H, s, CH$_3$-18), 0.93 (9H, s, t-BuSi), 0.95 (3H, d, J=7 Hz, CH$_3$-21), 1.26 (3 H, t, J=7 Hz, CH$_3$ of ester), 3.82 (1H, m, CH-3), 4.12 (2 H, q, J=7 Hz, CH$_2$ of ester), 4.64 (1H, s, CH$_A$-19), 4.92 (1H, s, CH$_B$-19), 5.84 (1H, d, J=12 Hz, CH-7), 6.45 (1H, d, J=12 Hz, CH-6).

EXAMPLE 12

6(R,S)-SO$_2$ adduct of Ethyl 1(S),3(R)-Bis(tertbutyldimethylsilyloxy)-9,10-seco-26,27-bisnorcholesta-5(E),7(E),10(19)-trien-25-oate Procedure A: 250-mL, 3-necked round-bottomed flask equipped with a mechanical stirrer, argon inlet, and a condenser was charged with 17.23 g (0.263 tool) of zinc dust, 40 mL of 1:1 pyridine/tetrahydrofuran (the THF was distilled under argon from sodium benzyphenone ketyl), 12.78 g of pulverized nickel chloride hexahydrate and 25.8 mL of ethyl acrylate. The stirred mixture was heated to 65°–70° C. for 30 minutes to give an orange-colored mixture, cooled to room temperature and treated with a solution of 40.0 g of the C-22 iodides (from Example 3) in 40 mL of 1:1 pyridinetetrahydrofuran. The mixture was stirred at 45° C. for 1.5 hours. As TLC (1:4 ethyl acetate/hexane) showed only ca. 50% conversion of iodides into products, 4.0 g of nickel chloride hexahydrate and 5.0 mL of ethyl acrylate were added. Stirring was continued at 45° C. for a further 3.5 hours and the reaction mixture was stored under argon at 0° C. overnight (18 hours). It was diluted with 70.0 mL of ethyl acetate and filtered through Celite, which was washed with 3×100 mL portions of ethyl acetate. The combined filtrate and washings were washed with 200 mL ice-cold 1N hydrochloric acid, 3×250 mL, of saturated brine (some emulsion), dried (MgSO$_4$), filtered and evaporated to give 40.7 g of 6(R,S)-SO$_2$ adduct of ethyl 1(S),3(R)-bis(tertbutyldimethylsilyloxy)-9,10-sec-26,27-bisnorcholesta-5(E),7(E),10(19)-trien-25-oate as a foam. TLC (silica gel, 1:1 ethyl acetate-hexane) showed the desired products at Rf 0.57 and Rf 0.45. The starting iodides had Rf 0.71 and Rf 0.51. The mixture of crude esters was converted directly into the triene as described in Example 13A. In a separate experiment, a batch of isomeric mixture of (3.3 g) in 10 mL of 5% ethyl acetate in hexane was purified by chromatography over 60 g of flash silica gel (40 μm) packed in 5% ethyl acetate and eluted with 10% ethyl acetate in hexane collecting 30 mL fractions. Isomer A(1.7 g) appeared in fractions 14–22, whereas, pure isomer B appeared in fractions 31–42 (437 mg). The progress of the chromatography was monitored by TLC (20% ethyl acetate in hexane). Isomer A;. This was obtained as an amorphous solid: mp 68°–70° C.; [α]$_D$+19.09° (CHCl$_3$, C=0.958); UV 202 (ε=22210), 266 (ε=230) nm; IR (CHCl$_3$) 1722 cm$^{-1}$; $^1$H NMR (CDCl$_3$) δ 0.05 (12 H, 2 x Me$_2$Si), 0.64 (3H, s, CH$_3$-18), 0.85 (18 H, 2 x t-BuSi), 0.95 (3H, d, J=6 HZ, CH$_3$-21), 1.25 (3H, t, CH$_3$ of ester), 3.61 (1H, d, J =12 Hz, CH$_A$ of CH$_2$SO$_2$), 3.95 ( 1H, d, J=12 Hz, CH$_B$ of CH$_2$SO$_2$), 4.12 (2H, q, J=7 Hz, CH$_2$O of ester), 4.18 (1H, br s, CHOSi), 4.36 (1H, br s, CHOSi), 4.65 (2H, q, CH-7+CH-6); MS 658 (M-SO$_2$). Isomer B: This was obtained as a gum, [α]$_D$−19.76° (CHCl$_3$, C=0.6830). Procedure B: A 100-mL, 3-necked, round-bottomed flask equipped with a mechanical stirrer, thermometer, and condenser capped with an argon inlet bubbler was charged with 20 mL of pyridine, 2.38 g of pulverized nickel chloride hexahydrate, 3.27 g zinc dust and 4.88 mL of ethyl acrylate. The mixture was stirred at 60° C. under argon for 30 minutes whereupon it became deep red. It was cooled to room temperature (23° C.) and treated with a solution of 7.49 g of iodides (from Example 3) 10 mL of pyridine. A slight exotherm (23° C.→28° C.) ensued. The mixture was stirred at room temperature for 2.5 hours, diluted with 50 mL of ethyl acetate and filtered over Celite. The Celite was washed with 100 mL of ethyl acetate and the combined filtrate and washings were washed sequentially with 100 mL of saturated brine: water (1:1), 200 mL of 1.0N hydrochloric acid, 100 mL of 1.0N hydrochloric acid, 100 mL of saturated brine, dried (MgSO$_4$), filtered and evaporated to give 7.22 g of a pale yellow foam. Chromatography of this on 95 g of silica gel packed in hexane, and elution and elution with 3% ethyl acetate in hexane then 5% ethyl acetate in hexane with monitoring of the chromatography by TLC, gave, after evaporation of the solvents, 5.28 g of 6(R,S)-SO$_2$ adduct of ethyl 1(S),3(R)-bis(tertbutyldimethylsilyloxy)-9,10-seco-26,27-bisnorcholesta-5(E),-7(E),10(19)-trien-25-oate.

EXAMPLE 13

Ethyl 1(S),3(R)-Bis(tert-butyldimethylsilyloxy)-9,10-seco-26,27-bisnorcholesta-5(E),7(E),10(19)-triene-25-oate A. A 1-L, 3-necked, round-bottomed flask equipped with a mechanical stirrer and a condenser capped with an argon inlet bubbler was charged with 39.2 g of the crude mixture of esters and (from Example 12) in 300 mL of 95% 2B alcohol and 20.4 g of sodium bicarbonate. The mixture was stirred at reflux for 2.25 hours, cooled to ca. 45° C. and concentrated in vacuo. 100 mL of ethyl acetate followed by 250 mL of hexane were added, and the mixture was stirred for 30 minutes. It was filtered and the filter cake was washed with 2×50 mL of hexane. The combined filtrate and washings were evaporated to give 36.8 g of a yellow semi-solid. This was dissolved in some hexane and applied to a column of 380 g of silica gel 60 (230–400 mesh) and eluted with 1%, 3%, 5%, and 10% methylene chloride in hexane to remove some less polar impurities as revealed by TLC (1:1 CH$_2$Cl$_2$ in hexane), and finally with 10% ethyl acetate in hexane to give, after collection of the appropriate fractions (ascertained by TLC, 50% CH$_2$Cl$_2$ in hexane) and evaporation (water aspirator then high vacuum) 20.73 g of ethyl 1(S),3(R)-bis(tert-butyldimethylsilyloxy)-9,10-seco-26,27-bisnorcholesta-5(E),7(E),10(19)-triene-25-oate as a colorless, waxy solid: mp 69°–71° C.; [α]$^{25}$D+51.35° (CHCl$_3$, C=0.9192). UV (EtOH) 268 (ε=24220) nm; IR (CHCl$_3$) 1725, 835 cm$^{-1}$; MS m/z (M$^+$, 12). Anal. Calcd for C$_{39}$H$_{70}$O$_4$Si$_2$; C, 71.06; H, 10.70. Found: C, 71.19; H,10.95.

B. A 50-mL, round-bottomed flask equipped with a condenser capped with an oxygen inlet bubbler, addition funnel, and containing a magnetic stirrer bar was charged with 550 mg of nickel chloride hexahydrate, 10 mL of pyridine, 760 mg of zinc powder, and 1.16 mL ethyl acrylate. The mixture was stirred at 55°–60° C., ca. 5 mg of iodine was added, and stirring was continued at 55°–60° C. for 20 minutes to give a dark red heterogeneous mixture. It was cooled to 40° C., and treated with a solution of 1.59 g of the iodide from Example 5 in 5 mL of pyridine, stirred at room temperature for 45 minutes, and diluted with 60 mL of ethyl acetate. The mixture was filtered over Celite, and the filtrate was washed with 50 mL of water, 50 mL of 1.0N hydrochloric acid, 50 mL of saturated brine, dried (MgSO$_4$), filtered, and evaporated to give a gum. Flash chromatography of which ever 25 g of silica with 1% ethyl acetate in hexane gave, after collection of the appropriate fractions and evaporation, 1.18 g (77%) of ethyl 1(S),3(R)-bis(tert-butyldimethylsilyloxy)-9,10-seco-26,27 -bisnorcholesta-5(E),7(E),10(19)-triene-25-oate as a gum, identical with the sample from Example 13 A.

C. 31 g of the compound from Example 11 dissolved in 280 mL of (1:1)methanol-dichloromethane, 13.8 g of N-methylmorpholine-N-oxide and 2.30 g of selenium dioxide was heated at reflux under argon for 5 hours. The mixture was cooled and concentrated in vacuo to one third of the volume. Then 1.0 L ethyl acetate was added, and the mixture was washed with 3×500 mL=1.5 L of 1:1 brine-water and 500 mL brine, dried (Na$_2$SO$_4$) and evaporated to dryness to afford 33 g of a crude mixture which dissolved in 500 mL dichloromethane and treated with 6.1 g imidazole and 9.8 g of t-butyldimethylsilyl chloride. The mixture was stirred at room temperature under argon for 16 hours. The insolubles were filtered off, rinsed with 2×150 mL of dichloromethane and the filtrate and washings were evaporated to dryness. The residue was taken up in 1.0 L of ethyl acetate and washed with 3×500 mL of 1:1 brine water and 500 mL of brine, dried (Na$_2$SO$_4$) and evaporated in vacuo, and finally at 0.5 mm Hg for 2 hours, to afford 38.6 g crude product. This was dissolved in 50 mL dichloromethane-hexane (1:2) and applied to 400 g of flash silica gel (200–400 mesh) prepacked in dichloromethane hexane (1:2). Elution at 4 psi air pressure with 20×250 mL of 1:2 dichloromethane hexane followed by 4×500 mL of 3:1 dichloromethane hexane. Fractions 7–20 were combined and evaporated in vacuo, finally at 0.5 mm Hg affording 15.85 g (41% yield over 2 steps) of ethyl 1(S),3(R)-bis(tertbutyl-dimethyl-silyloxy)-9,10-seco-26,27-bisnorcholesta-5(E),7(E),10(19)-triene-25-oate as a colorless amorphous solid, identical with the samples prepared in Examples 13 A and 13 B.

EXAMPLE 14

6(R,S)-SO$_2$ adduct of 3(R)-tertbutyldimethyl-silyloxy-25-keto-9,10-seco-cholesta-5(E),7(E),10( 19)-triene A 100-mL three-necked flask equipped with a magnetic stirrer and a gas bubbler was charged with 2.24 g of zinc dust suspended in 16 mL of 1:1 mixture of tetrahydrofuran-pyridine. To this suspension were added 4.10 g of nickel chloride hexahydrate and 3.0 mL of methyl vinyl ketone while the reaction mixture was slowly heated to 65° C. After 30 minutes of heating at 65° C., the mixture was cooled to 35° C. and a solution of 10.6 g of C-22-iodo SO$_2$ adduct t-butyldimethylsilyl ether from Example 1 in 12 mL of 1:2 mixture of tetrahydrofuran-pyridine was added over a 10 minute period. The reaction mixture was stirred for 2 hours at ambient temperature. TLC (7:3 hexane-ethyl acetate) indicated that the reaction was complete. The mixture was diluted with 250 mL ethyl acetate and filtered through a Celite pad using a sintered glass funnel. The filtrate was washed with 3×100 mL=300 mL EDTA solution (80 g EDTA+80 g NaHCO$_3$ diluted to 1.0 L), 2×100 mL=200 mL 1:1 brine-water, dried (Na$_2$SO$_4$), evaporated in vacuo on the rotary evaporator, finally at 0.5 mm Hg for 2 hours to afford 11 g of crude 6(R,S)-SO$_2$ adduct of 3(R)-tertbutyldimethyl-silyloxy-25-keto-9,10-secocholesta-5(E),7(E),10(19)-triene which was used directly in the next step (Example 15).

EXAMPLE 15

3(R)-tert-Butyldimethylsilyloxy-25-keto-9,10-seco-cholesta-5(E),7(E),10(19)-triene A mixture of 11.0 g of C-25-ketone SO$_2$-t-butyldimethylsilyl ether from Example 14, 4.1 g of sodium bicarbonate, and 55 mL of 95% ethanol was refluxed under argon for 2 hours. TLC (9:1 hexane-ethyl acetate) indicated that the reaction was complete. The reaction mixture was diluted with 250 mL of ethyl acetate and washed with 3×100 mL of 1:1 brine-water and 2×100 mL=200 mL of brine, dried (Na$_2$SO$_4$), and evaporated to dryness. The crude residue was chromatographically purified to afford 5.35 g (62% yield for the two steps) of 3(R)-tert-Butyldimethylsilyloxy-25-keto-9,10-seco-cholesta-5(E),7(E),10(19)-triene.

EXAMPLE 16

1(S,R)-Hydroxy,3(R)-tertbutyldimethylsilyloxy-25-keto-9,10-secocholesta-5(E),7(E),10(19)-triene 2.35 g of the C-25-ketone trans-triene t-butyldimethylsilyl ether, from Example 15 in 1.10 g of N-methylmorpholine-N-oxide, and 0.26 g of selenium dioxide were dissolved in 30 mL of (1:1) mixture of methanol-dichloromethane. The mixture was heated at reflux under argon for 2 hours and tlc (4:1 hexane-ethyl acetate) indicated that the reaction was complete. The reaction mixture was then concentrated to one third of its volume, diluted with 150 mL ethyl acetate and washed with 3×125 mL=375 mL of 1:1 brine-water, 125 mL of brine, dried (Na$_2$SO$_4$), evaporated to dryness, and finally at 0.5 mm Hg to afford 2.4 g crude mixture of 1(S,R)-hydroxy, 3(R)-tertbutyldimethyl-silyloxy-25-keto-9,10-secocholesta-5(E),7(E),10(19)-triene which was used as such in the next step. (Example 17).

EXAMPLE 17

1(S),3(R)-Bis(tertbutyldimethylsilyloxy)-25-keto-9,10-secocholesta-5(E),7(E),10(19)-triene A crude mixture (2.4 g) of 1α- and 1β-hydroxy compounds from Example 16 in 50 mL of dichloromethane, was treated with 0.5 g of imidazole and 0.9 g of t-butyldimethylsilyl chloride. The mixture was stirred at room temperature under argon overnight. The insolubles were filtered off, rinsed with 2×50 mL of dichloromethane, and evaporated to dryness. The residue was dissolved in 125 mL of ethyl acetate, washed with 3×50 mL of 1:1 brine-water, 50 mL of brine, dried (Na$_2$SO$_4$), evaporated in vacuo, and finally at 0.5 mm Hg for 2 hours to afford 2.9 g of crude product. This was dissolved in 3 ml, of dichloromethane-hexane (1:1) and applied to 300 g of Baker flash silica gel (200–400 mesh) pre-packed in dichloromethane-hexane (1:1). Elution at 4 psi air pressure with 30×125 mL of 1:1 dichloromethane-hexane followed by 16×125 mL of 2:1 dichloromethane-hexane. Fractions 18–29 were combined and evaporated in vacuo, finally at 0.5 mm Hg afforded 1.03 g (35% yield over 2 steps) of 1(S),3(R)-bis(tert-butyldimethylsilyloxy)-25-keto-9,10-secocholesta-5(E),7(E),10(19)-triene. This was converted into 1(S),3(R)-bis(tert-butyldimethylsilyloxy)-9,10-seco-25-hydroxycholesta-5(E),7(E),10(19)-triene with methyl magnesium bromide as described in Example 19.

EXAMPLE 18

Ethyl 1(S),3(R)-Bis(tert-butyldimethylsilyloxy)-9,10-seco-26,27-bisnorcholesta-5(Z),7(E),10(19)-trien-25-oate A 1-L photochemical reactor was charged with a solution of 913 mg of ester from Example 13 and 16-7 mg of 9-acetyl-antharcene in 1.0 L g hexane. With argon bubbled through it, the solution was cooled to 0°–5° C., and was irradiated with a 450 W medium pressure lamp for 45 minutes. The solution was concentrated to give 925 mg of ethyl 1(S),3(R)-bis(tert-butyl-dimethylsilyloxy)-9,10-seco-26,27-bisnorcholesta-5(Z),7(E),10(19)-trien-25-oate: $^1$H NMR (CDCl$_3$) δ 0.05 (12 H, 2 x Me$_2$Si), 0.55 (3 H, s, CH$_3$-18), 0.85 (18 H, 2 x t-BuSi), 0.95 (3 H, d, J=6, CH$_3$-21), 1.21 (3 H, t, J=7 Hz, CH$_3$ of ester), 4.10 (2 H, q, CH$_2$ of ester), 4.16 (1 H, br s, CHOSi), 4.39 (1 H, br s, CHOSi), 4.88 (1 H, s, CH$_A$-19), 5.18 (1 h, s, CH$_B$-19), 6.0 (1 H, d, J=11 Hz, CH-7), 6.24 (1 H, d, J=11 Hz, CH-6). This material was reacted with methylmagnesium bromide using conditions in Example 19, and the derived alcohol was desilylated with tetrabutylammonium fluoride using conditions defined in Example 21 to give calcitriol.

EXAMPLE 19

1(S),3(R)-Bis(tert-butyldimethylsilyloxy)-9,10-seco-25-hydroxycholesta-5(E),7(E),10(19)-triene 15.85 g of ester from Example 13 dissolved in 75 mL of dry tetrahydrofuran (distilled over Na benzophenone ketyl) was cooled in an ice bath. To the stirred solution was added 20 mL (0.060 mole) of methyl magnesium bromide (3.0M in ether) over 5 minutes. The mixture was stirred for 15 minutes. The ice bath was removed and stirring continued at ambient temperature for 3 more hours. The zero mixture was cooled to 0° C. and carefully quenched with 8 mL of saturated ammonium chloride. This mixture was diluted with 800 mL of ethyl acetate, and then washed with 3×250 mL of 1:1 brine water and 250 mL of brine, dried (Na$_2$SO$_4$), and evaporated in vacuo to afford 15.8 g of crude product. This was subsequently dissolved in 15 mL of ethyl acetate and applied to a 350 g of flash silica gel (200–400 mesh) column pre-packed in 4:1 hexane ethyl acetate. Elution at 4 psi air pressure with 15×125 mL=2.25 L of 4:1 hexane-ethyl acetate. Fractions 5–13 were combined and evaporated in vacuo and finally at 0.5 mm Hg for 2 hours to afford 12.7 g (82% yield) of 1(S),3(R)-bis(tert-butyldimethylsilyloxy)-9,10-seco-25-hydroxy-cholesta-5(E),7(E),10(19)-triene as a colorless foam. $[α]^{25}$D+35.14°; UV (EtOH), 269 (ε=22, 520) nm; IR (CHCl$_3$) 3605 and 1730 cm$^{-1}$; $^1$H NMR (CDCl$_3$) δ 0.05 (12 H, 2 x Me$_2$Si), 0.55 (3 H, s, CH$_3$-18), 0.85 (9 H, s, t-BuSi), 0.90 (9 H, s, t-BuSi), 0.95 (3 H, d, J=7 Hz, CH$_3$-21), 4.22 (1 H, br s, CH OSi), 4.55 (1 H, br s, CHOSi), 4.93 (1 H, s, CH$_A$-19), 4.99 (1 H, s, CH$_B$-19), 5.82 (1 H, d, J=11 Hz, CH-7), 6.46 (1 H, s, CH-6); MS m/z 644 (1, M+).

EXAMPLE 20

1(S),3(R)-Bis(tert-butyldimethylsilyloxy)-9,10-seco-25-hydroxycholesta-5(Z),7(E),10(19)-triene 12.5 g (0.0194 mole) of alcohol from Example 19 dissolved in 800 mL of methanol containing 3 mL of triethylamine and 630 mg of thioxanthen as sensitizer, was irradiated using a 450 Watt Hanovia lamp for 2 hours. The reactor was emptied and rinsed with 2×100 mL=200 mL of methanol. The mixture was evaporated in vacuo. The residue was dissolved in 100 mL of 1:1 dichloromethane-ethyl acetate, concentrated to a third volume, and applied to a 500 g flash silica gel (200–400 mesh) column packed in 4:1 hexane-ethyl acetate. The column was eluted at 4 psi air pressure with 20×125 mL of 4:1 hexane-ethyl acetate. Fractions 7–15 were combined, evaporated in vacuo to dryness, finally at 0.5 mm Hg for 2 hours to afford 11.7 g (93% yield) of 1(S),3(R)-bis(tert-butyldimethylsilyloxy)-9,10-seco-25-hydroxy-cholesta-5(Z),7(E),10(19)-triene as a colorless amorphous solid. $^1$H NMR (CDCl$_3$) δ 0.05 (12 H, 2 x Me$_2$Si), 0.55 (3 H, s, CH$_3$-18) 0.85 (18 H, 2 x t-BuSi), 0.92 (6 H, s, CH$_3$-26+CH$_3$-27), 4.20 (1 H, br s, CHOSi), 4.38 (1 H, br s, CHOSi), 4.84, (1 H, s, CH$_A$-19), 5.8 (1 H, s, CH$_B$-19), 6.04 (1 H, d, J=11 Hz, CH-7), 6.24 (1 H, d, J=11 Hz, CH-6).

EXAMPLE 21

1(S),3(R),25-Trihydroxy-9,10 secocholesta-5(E),7(E),10(19)-triene

A 1-L, 3-necked, round-bottomed flask equipped with a mechanical stirrer and argon inlet was charged with a solution of 19.01 g of the compound from Example 19 in 50 mL of anhydrous tetrahydrofuran and 337 mL of a 1.0 molar solution of tetrabutylammonium fluoride. The solution was stirred at room temperature fro 5.5 hours, concentrated in vacuo at 45° C., and the resulting thick amber colored oil, which was partitioned between a mixture of 500 mL of ethyl acetate and 500 mL of a 1:1 water-saturated brine. The organic phase was separated, and the aqueous phase was extracted with 2×250 mL of ethyl acetate. The combined organic extracts were washed with 3×250 mL of 1:1 water-saturated brine, dried (MgSO$_4$), and carefully evaporated at 50° C. to give 16.06 g of an off-white solid. This was slurried with 100 mL of 30% ethyl acetate in hexane left at 0° C. overnight and the product was collected by filtration. It was washed with 3×20 mL 50% ethyl acetate in hexane, and dried in vacuo to give 9.94 g (81%) of 1(S), 3(R),25-trihydroxy-9,10-secocholesta-5(E),7(E),10(19)-triene: mp 170°–173° C.; [α] D+164.39° (CHCl$_3$, c=0.925).

EXAMPLE 22

1α,25-Dihydroxycholecalciferol(Calcitriol)

A. From 1α, 3β-Bis(tertbutyldimethylsilyloxy)-9,10-seco-25-hydroxycholesta-5(Z),7(E),10(19)-triene. To a solution of 11.5 g of alcohol from Example 20 in 25 mL of tetrahydrofuran (distilled over Na benzophenone ketyl) was added a solution of 41 mL of tetrabutylammonium fluoride (1.0M in THF). The reaction mixture was stirred at 45° C. for 4 hours under argon. TLC (3:7 hexane-EtOAc) indicated the reaction was complete. The mixture was evaporated in vacuo to dryness. The residue was taken up in 600 mL of ethyl acetate and washed with 3×200 mL of 1:1 brine-water and 200 mL of brine, dried ($Na_2SO_4$) and evaporated in vacuo to afford 12.0 g of crude product. This was dissolved in 15 mL of 3:7 hexane-ethyl acetate and applied to 200 g flash silica gel (200–400 mesh) column packed in 3:7 hexane-ethyl acetate. Elution with 24×125 mL 3:7 hexane-ethyl acetate, and 2×500 mL ethyl acetate at 4 psi air pressure. Fractions 10–26 were combined and evaporated in vacuo to afford 6.87 g of calcitriol as a colorless foam. Recrystallization from 30 mL of methyl formate afforded 5.30 g of calcitriol as colorless needles, mp 110°–113°,$[\alpha]^{20}$ D= +49.13° (c=1.0, Ethanol).

B. From 1(S),3(R),25-Trihydroxy-9,10-seco-cholesta-5(E),7(E), 10(19)-triene. A 1.0 L, jacketed photochemical reaction was charged with 9.79 g of the compound from Example 21 and 0.43 g of 9-acetylanthracene in 1.0 L of methanol. Argon was passed through the cooled (0° C.) solution and irradiation was carried out at 0°–5° C. with a medium pressure 450 W Hanovia lamp through a uranium filter for 2.0 hours. The solution was transferred to a 3-L, round-bottomed flask and was concentrated at 45° C. to give a foam. This was dissolved in 30 mL of 70% ethyl acetate in hexane and the solution was applied to a column of 180 g of silica gel (40 μm) packed in 70% ethyl acetate in hexane. Elution collecting 100-mL fractions, was carried out under pressure with 1 L of 70% ethyl acetate in hexane (to remove a small amount of non-polar material), 1 L of 80% ethyl acetate in hexane, and finally 1 L of 90% ethyl acetate in hexane. The progress of the chromatography was monitored by TLC (30% hexane in ethyl acetate). The appropriate fractions were combined and evaporated to give 10.17 g of a foam, which was crystallized from 220 mL of methyl formate to give 6.5 g of calcitriol, mp 115°–116° C.; $[\alpha]^{25}D+45.5°$ (EtOH, c=1.059).

We claim:

1. A process for the preparation of a compound of the formula

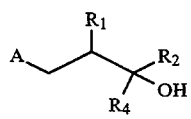

I' wherein A is a 23,24-bisnorsteroid or a 23,24-bisnor-9,10-secosteroid radical, $R_1$ is hydrogen, hydroxycarbonyl, lower alkoxycarbonyl, lower alkylcarbonyl or unsubstituted or substituted lower alkyl, $R_2$ is hydroxyl, lower alkoxy, or unsubstituted or substituted lower alkyl, and $R_4$ is lower alkyl, (1) which comprises reacting a compound of the formula

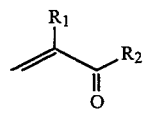

III with a nickel hydrate or, if unhydrated, in the presence of a proton source and a reducing agent; in the presence of an organic solvent and ligand source, and thereafter, (2) treating the reaction product of step 1, with a compound of the formula

AX   II wherein A is as previously described, and X is halogen to yield a compound of the formula

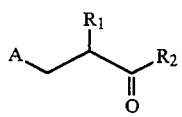

IV (3) reacting the compound of formula IV with an organometallic reagent which adds $R_4$, to yield the corresponding compound of formula I'.

2. A process according to claim 1 wherein the organometallic reagent is $R_4MgX$ and $R_4$ is lower alkyl and X is halogen.

3. A process according to claim 1 wherein the organometallic reagent is $R_4Li$ and $R_4$ is lower alkyl.

4. A process according to claim 1 wherein the compound of formula I is 1α,25-α, hydroxy cholecalciferol.

5. A process according to claim 1, wherein the nickel salt is nickel halide hydrate.

6. A process according to claim 5, wherein the reducing agent is zinc.

7. A process according to claim 6, wherein the compounds of formula II are

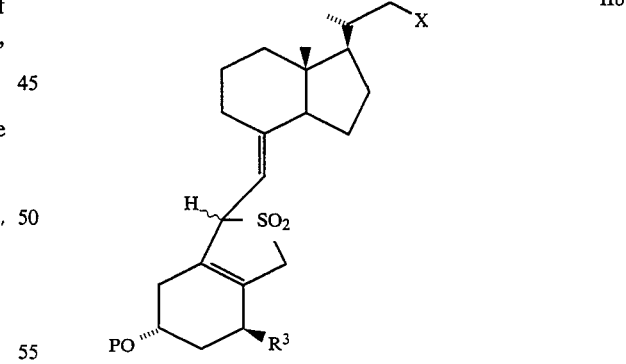

IIb wherein X is halogen, R3 is hydrogen or OP and P is hydrogen or a protecting group.

8. A process according to claim 7, wherein $R_3$ is hydrogen, X is iodine, and P is t-butyldimethylsilyl.

9. A process according to claim 8, wherein in the compound of formula III, $R_1$ is hydrogen and $R_2$ is lower alkyl or lower alkoxy.

* * * * *